United States Patent
Nguyen

(10) Patent No.: US 11,311,597 B2
(45) Date of Patent: Apr. 26, 2022

(54) WHITENED TURMERIC PRODUCT FOR THE PREVENTION OF VIRAL INFECTIONS

(71) Applicant: Bich Van T Nguyen, Bristow, VA (US)

(72) Inventor: Bich Van T Nguyen, Bristow, VA (US)

(*) Notice: Subject to any disclaimer, the term of this patent is extended or adjusted under 35 U.S.C. 154(b) by 25 days.

(21) Appl. No.: 16/873,162

(22) Filed: Feb. 18, 2020

(65) Prior Publication Data

US 2021/0252096 A1    Aug. 19, 2021

(51) Int. Cl.
| | |
|---|---|
| *A61K 36/9066* | (2006.01) |
| *A61K 9/06* | (2006.01) |
| *A61P 31/14* | (2006.01) |
| *A61K 9/00* | (2006.01) |

(52) U.S. Cl.
CPC .......... *A61K 36/9066* (2013.01); *A61K 9/006* (2013.01); *A61K 9/007* (2013.01); *A61K 9/06* (2013.01); *A61P 31/14* (2018.01)

(58) Field of Classification Search
None
See application file for complete search history.

(56) References Cited

U.S. PATENT DOCUMENTS

| | | | | |
|---|---|---|---|---|
| 6,048,533 | A * | 4/2000 | Nguyen ............. | A61K 36/9066 424/401 |
| 2004/0234546 | A1* | 11/2004 | Lieberman ............. | A61K 36/84 424/195.18 |
| 2010/0330205 | A1* | 12/2010 | Nakamori ............... | A61P 31/04 424/687 |
| 2012/0107429 | A1* | 5/2012 | Lee ....................... | A23L 33/105 424/756 |

* cited by examiner

*Primary Examiner* — Ralph J Gitomer
(74) *Attorney, Agent, or Firm* — Thrive IP ®

(57) ABSTRACT

A method of preventing and treating viral infections, in particular infections caused by the Corona virus are disclosed. The method involves applying a syrup containing a whitened turmeric product to the throat of a person. The syrup traps viruses in the throat and prevents further dissemination through the air, as well as reaching the person's airways. Thus, the trap works both ways.

4 Claims, 2 Drawing Sheets

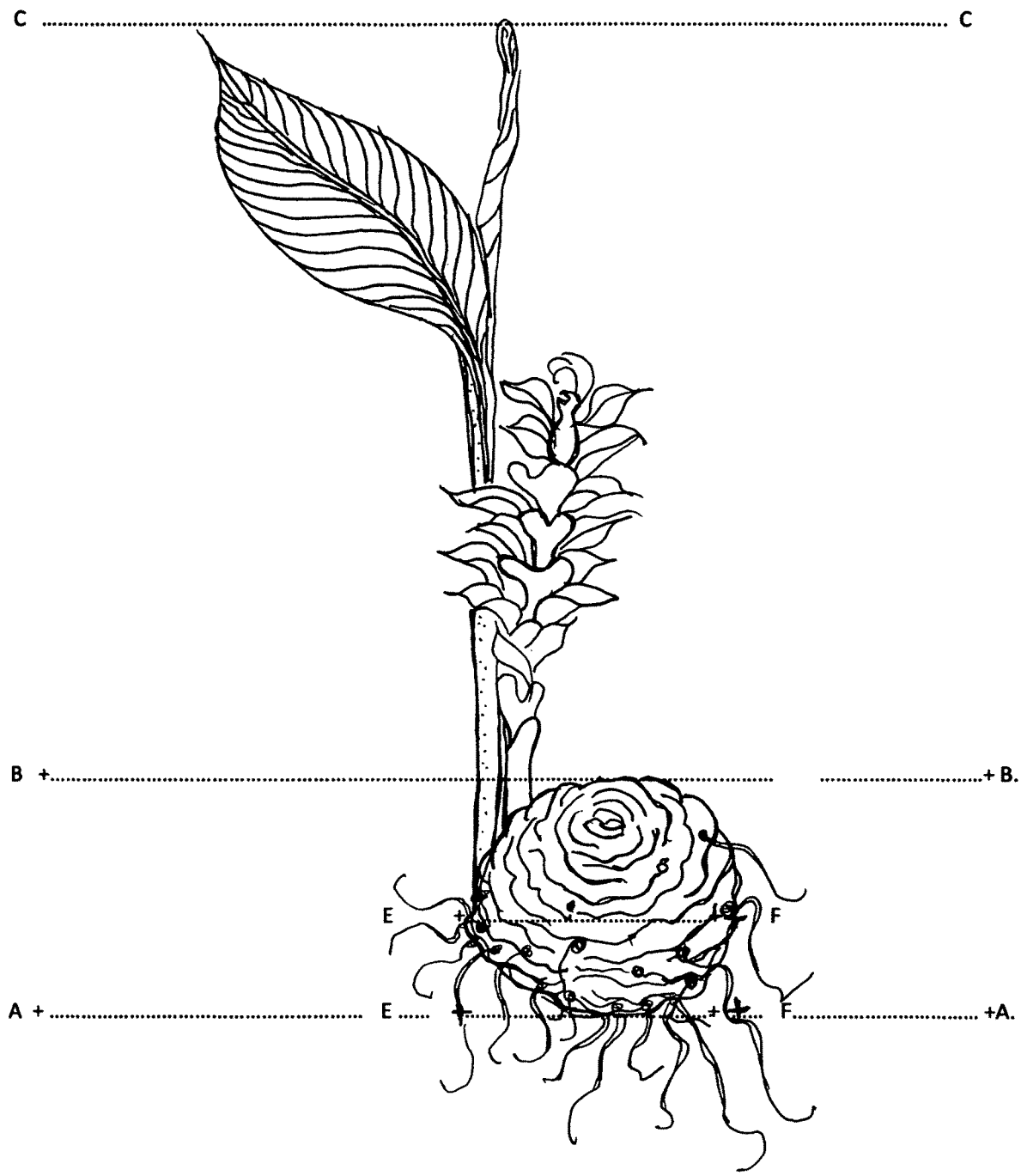
FIG 1 : White Turmeric Plant with Round ball shape root.

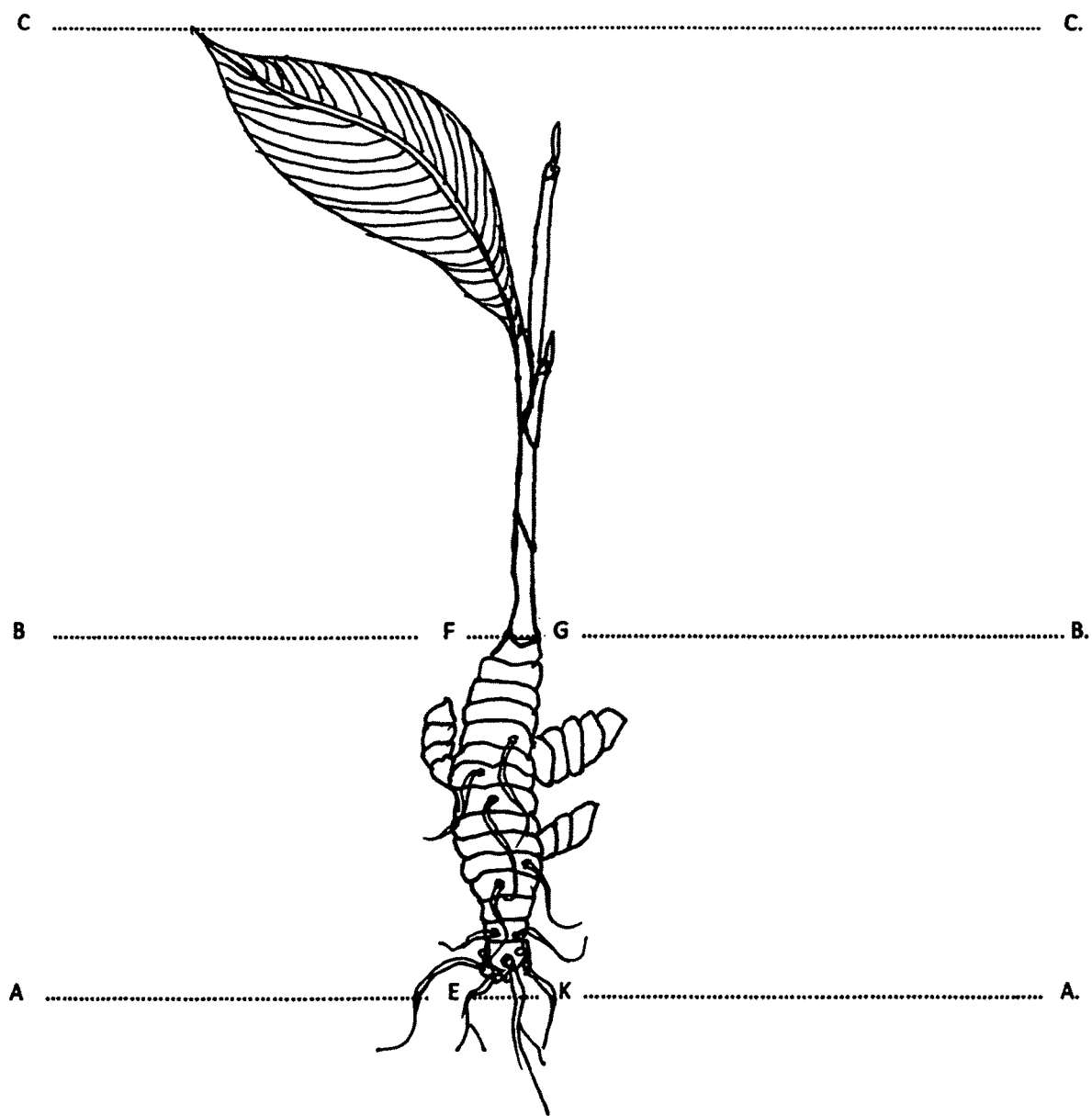
FIG 2 : White Turmeric Plant with fingertip shape root.

WHITENED TURMERIC PRODUCT FOR THE PREVENTION OF VIRAL INFECTIONS

FIELD OF THE INVENTION

This present invention relates to whitened turmeric products for the treatment, prevention, and cure of Covid-19 infections and to prevent the spread of Covid-19.

BACKGROUND OF THE INVENTION

Treatments with white turmeric are known from U.S. Pat. No. 5,897,865 to Nguyen, filed Apr. 27, 1999, U.S. Pat. No. 6,048,533 to Nguyen, filed Sep. 1, 1999, and U.S. patent application Ser. No. 16/602,060 to Nguyen, filed Aug. 1, 2019.

Turmeric, and generally turmeric treatment and the whiten turmeric products have been in use for 20 years. They worked and helped in many cases involving infection, diseases caused by bacteria and viruses, such as: bad breath, gums disease, cold sore, cancer sore, sinus, eye, ear infection, sore throat, chronic cough, lung disease, lung cancer, lung infection, tongue cancer, allergies, sinus infections, flu, stomach ulcer, stomach virus and many other infections or skin conditions, such as: acne, eczema, psoriasis, hemorrhoids, cuts, burns, insect bites, poison ivy and many more. Turmeric products have no side effects. As a natural treatment they support health recovery and healing.

Turmeric has been used as a cooking spice with a yellow color and as traditional medicine for many years. The following disclosure describes the turmeric root. White turmeric root and whitened turmeric products have been in use for 20 years. As a natural treatment it provides an effective amount in the ingredients and a method how it is made and used for ailments, chronic infection, disease, tumor's, cancer, etc. is shown. The discovery of the medical method treatment technique with the product of whitened turmeric syrup is shown. It is one of the best products and can be used for many issues.

The products have natural benefits: anti-bacteria, anti-inflammation, anti-infection, antioxidant and pain relief. A useful product works as a trap, can be used daily, stays well in all wet glands and infection areas, in the nose, eye, can get deep inside the ear and cleans up very well. Many cases achieved healing and do not require any drugs or a specialist. With regard to the infection in the mouth or throat, turmeric syrup can be re-applied after any meal and drink. The treatment for pain relief, sneeze and cough, it can work miracles in 5 minutes to an hour. Also, it is a trap which can trap and kill bacteria and viruses. The sticky turmeric adheres in all infection areas, where a lot of trouble can be caused by bacteria, toxins, toxic chemicals, viruses, etc. . . . . The sticky turmeric product processes them into waste, which will begin detoxing through discharge of feces and urine after 21 days. All detoxing will process to the final step, and all the infection areas can get clean and heal very well. It also can help other tissues and organs at the same time. It works as a body cleaner and blood cleanser.

A new look has been taken to adapt these treatments for Covid-19. It is used as a cure and for prevention. Over many years, the inventor has recovered and healed from many illnesses. Thus, the need to visit a doctor, take drugs or go to the hospital can be eliminated.

Having worked with white turmeric for 20 years, the many experiences the inventor had with whitened turmeric have been supporting the inventor in looking for the cure, treatment, prevention and control of the spread of Covid-19.

OBJECT OF THE INVENTION

It is an object of the invention to discover a cure of Covid-19 for which no cure has been previously found. When a lot of people were suffering with coughing, sneezing and spreading of the virus, the illness, the contagiousness, the infection and the hopeless become an issue. It relates to our lives, our businesses, and our world's health problems. the instant method can treat the coughing and sneezing in an easy manner. It can trap all the viruses and cleanup all infection areas and the lung by a simple detoxing process for the Corona virus. Covid-19 is a serious issue.

SUMMARY OF THE INVENTION

A trap for viruses is provided. Turmeric Syrup has been used since the year 2000 in many tests to prove it acts as an anti-bacterium. For the test two of the same items are provided. Ex: 2 pieces of fish, 2 pieces of beef, 2 shrimps or 2 small cups of soup. One piece is covered or immersed deep inside the turmeric syrup and then taken out and the other one is not. Day by day the two pieces have been observed and it was found the turmeric syrup can be used for food protection so well. On the 3rd day, the 4th day or the 9th day, odors emanating from the piece without the turmeric syrup cover, i.e., the piece of fish, beef or shrimp get have a stronger smell, and it can be seen that a lot of moving bacteria are on them through the microscope. The soup can be seen to build up mold on top within days. However, the piece that has turmeric syrup still looks fresh on the 3rd day, and always much better than the other piece every day when compared to each other. These simple tests can prove or help the understanding of the anti-bacterial benefit from the whitened turmeric syrup product. It was a dirty job to keep testing and trying to examine these stinky pieces under the microscope.

One day, a lot of maggots were found in the trash can, which came from the sea food: in the clam and crab shells. The trash can was cleaned up and a lot of maggots were collected to get the test ready. The whitened turmeric syrup was squeezed on the platform, then tried to be poured over the maggots on top. But it was not enough for all, a lot of maggots escaped by moving away quickly. It was tried to squeeze more turmeric, a lot more, as much as possible on them. The test does not need the microscope, maggots were moving and dying in the trash can, some maggots could get out but were covered by the turmeric syrup, could not move much and were dying too. The test can prove how the whitened turmeric syrup can be used to trap bacteria, viruses, and life forms as big as maggots that are dying from the whitened turmeric syrup.

Since 2000, the inventor has made turmeric syrup and turmeric cream and lotion. The selection of all ingredients in each product is not an easy choice, because it relates to the safety and ease of use on skin, scalp, face and how it can safely used to work inside the eyes, nose, ear having an infection, ulcer or cancer.

The whitened turmeric base used for all turmeric product and is always the most important ingredient, which is described in U.S. Pat. No. 6,048,533 issued on Apr. 11, 2000. Many tests for ingredients were performed and testing was conducted many times to experience and use each product. People may be concerned about the use of bleach and possible side effects, so the whitened turmeric base was rinsed several times to prevent the side effect. Another choice was to test and work on turmeric roots having a natural white color. Working diligently, the final ingredients for each product are as follows. Turmeric capsules contain 400 mg/each. Whitened turmeric syrup has 10 to 12 percent of whitened turmeric base, whitened turmeric lotion has 3 percent of whitened turmeric base and whitened turmeric cream has 2 percent of whitened turmeric base. It was found to be the best choice of ingredients and works very well at all areas having an infection or a cut to the skin, bleeding, burn, itching, insect bites, poison ivy, acne, eczema, psoriasis, pain, migraine, and headache, and is safe for all users. In some cases, the mixture of two products, turmeric syrup and turmeric cream or lotion can help faster healing and is more comfortable. Whitened turmeric is a very sticky item comparable to glue.

BRIEF DESCRIPTION OF THE DRAWINGS

FIG. 1 shows a white turmeric root with round shape. The size can be up to 15 cm with a round circumference and 14 cm high. The weight can be up to 22 ounces. The plant height can be up to 7 feet. It can flower in spring or late in fall with white color and some yellow in the center.

FIG. 2 shows a white turmeric root with a finger shape. The size can up to 9 cm high times 1.8 cm with a round circumference. The weight can be up to 11 ounces. the height of the plant can be up to 5 feet with a round shape.

These roots are the most important ingredient to make white or whitened turmeric syrup, which will be used as a trap for Coronavirus treatment and prevention. Also, in the turmeric roots are the ingredients for whitened turmeric cream or lotion, which can be used for many cases related to the infection caused by Coronavirus. The product is used for prevention, trapping, treatment against any virus in their track.

FIG. 1 and FIG. 2 show two kinds of natural turmeric roots with the white color instead of the yellow or orange color. They are from the turmeric plant family.

White turmeric product and whitened turmeric product are similar. It is not much different how to make and use them.

Finally, over the last two years, the inventor has procured a lot more of white turmeric roots. They were enough for conducting testing in many cases several times. Each kind— the round shape or the fingertip of white turmeric roots— were used as ingredient for the whitened turmeric syrup product by themselves. The whitened turmeric syrup works well against bad breadth and cough. The whitened turmeric cream or lotion works in all infection area by itself or in a mix with whitened turmeric syrup.

White and whitened turmeric products look the same and have mostly similar benefits.

It was found from many tests that they can be mixed with the ingredients and have the same benefit. These mixing with the other ingredient works very well. They have a special white color instead of the yellow color.

The other ingredients were mixed with the whitened turmeric product for the base. These bases work the same. All tests were about the natural white turmeric roots.

It is planned to provide white turmeric base in sufficient amounts for sale. Attempts are made to grow these plants a lot more such that these natural roots can be brought to the market.

Not much has changed in the ingredients for all turmeric products, but the experience from use has surprisingly increased the number of diseases that can be healed and cured. If only one, two or three cases works, it would still be a hope and not certain that the treatment works, but in 20 years many instances of healing cases, namely more than a hundred have been observed. Based on these experiences the treatment was adapted to use turmeric products against the Corona virus? It traps the Corona viruses as it has trapped the bacteria and maggots.

A trap for Corona virus, the turmeric product can be announced to the public as soon as possible because it is the world's health issue now. With all the experience from 20 years and many cases of healing from bad breath, chronic cough, sinus, eyes infection, ear infection, sore throat, gums disease, cold sore, cancer sore, flu, lung infection, lung cancer, asthma, stomach ulcer, stomach virus, skin infection, etc. were healed and cured. The same treatment is performed with turmeric capsule, turmeric cream, turmeric lotion, and turmeric syrup.

The turmeric syrup is one of the best products and can do most of the work for the healing. It is used as a trap. For example, the bad breath issue: 5 to 10 drops are applied after a meal and drink to trap all the foul-smelling bacteria and/or viruses in the mouth. Just a few days are needed for bad breath to be gone. It works the same with cold sore or gums disease. In the treatment against Corona virus, it is used as a trap for controlling the spreading of the virus from the mouth to of from another person by talking and coughing or if the virus accidently gets from another person or from the person's hands by bringing the Corona virus into the mouth. A trap is a preventive treatment. Between prevention and treatment after infection, whitened turmeric syrup is better used earlier for the prevention.

Ex 1: For the sore throat or cough, 5 to 10 drops are applied to the throat after meal and drink, the turmeric product will help to reduce the pain and cough within 5 to 30 minutes in the infection area, turmeric products can trap and kill all bacteria and viruses and tissue infections recover very well.

Ex 2: For sinus, bleeding nose, breathing issue and sneezing: lotion only or the mix of turmeric syrup with the cream or lotion are applied twice/a day. Pain relief will begin in 5 to 30 minutes in an infection area. Turmeric syrup can cover and fix the area causing the bleeding very well, also it can open the breathing airways and start to trap and kill all bacteria and viruses.

Ex 3 For the lung infection, disease or asthma, all products, namely capsule, syrup, cream and lotion are combined for use as a treatment. Oral intake, inhaling and topical application are used for detoxing. Many cases of cancer, water in the lung, or asthma, recovered and healed after detox detoxing.

A detox detoxing treatment invention was applied for in 2019. Detox and detoxing treatments were used for many years, without the experience of the use, some persons overdosed, some cannot take any capsule and so many other issues were a problem. At that time, the users shared their experience with excessive amounts of the turmeric capsule, extra turmeric syrup product, the cream and lotion with the hope that they could detox and the healing would be faster. But the detoxing was not going well. Absorption through the skin caused much worry with the pain and fever. It causes side effects on the skin with scary symptoms such as: swollen eyes, nose, ears or irritation of the face, neck, body, hands, legs and feet. It was scary and caused much worry in the early years from 2000.

At that time, it was thought that the side effects of the treatment stem from turmeric products. So, the use of the turmeric capsule was stopped in many cases involving skin issues and all these cases were followed to get the experience from each one. The collection and experience found from the information supported for each case that they all can get skin healing with doctor visits and the use of drugs such as amoxicillin, an anti-biotic, or a steroid. After these bad ways of detoxing, 50% reported that their chronic issues or skin, got better. If they stop using these turmeric capsules or turmeric syrup, their chronic infection, disease, health issue such as sore throat, bad breath, stomach ulcer pain, sinus infection, Flu, constipation, etc. came back, so they tried to continue using only whitened turmeric syrup products for oral intake and stop the oral intake of the turmeric capsules that took place earlier. Great news was adding up with many cases. Many cases reported healing and the inventor was pleased to have gone through the bad time: Detox detoxing through the skin. Which is the most stressful for some users and our response. It was deliberated why it happened which was a concern for years.

It took 5 years to get a clear picture and discover the reason for side effects caused by detox detoxing through the skin. About only 2% of cases of side effects occur with the group never having skin problems such as acne, itchy, eczema, psoriasis, etc. . . . . But the number goes up to 5% to 10% for people who have skin problems such as acne, itchy, eczema, or psoriasis and smoke cigarettes. And these people are in the group that buys and uses the turmeric capsule only.

These experiences were bad at times for users. But with time in a few years recorded, they all got better and recovered well. These facts were learned from our experience: That is not the side effect. It is the detox detoxing performed the wrong way. A lot of users were in an emergency and were treated and helped by doctors and drugs as steroid treatment at the hospital.

These experiences of recovery after nasty symptom on the skin were key. Because a lot of users shared how much better and their disease or chronic condition got much better and healed. This information helped and the detox detoxing in the final form, included how to use the turmeric product in a safe way.

Detox detoxing works as a body clean up and a blood cleanser. Then, the recovery and healing will begin. It is the invention, the discovery from turmeric product. Detox detoxing will be the simplest treatment for all issues, diseases, infection, tumor, cancer and will be a preventive treatment against Covid-19.

What this experience means, my invention will be the treatment for COVID-19.

White turmeric roots and whitened turmeric products can be made with experience and are safe for use.

And it is especially the discovery of how to use them for safe detox detoxing.

The experience from many cases has helped to understand all steps: provide a trap, the collection time for all the waste is 20 days, and detox detoxing occurs at the 21$^{st}$ day from the treatment start.

This invention and discovery of all steps was not easy from the beginning. It took years and stressful experiences because all the detox detoxing happens through the skin.

It is still not known what it is or what will happen after the skin is freed from all infection by detox detoxing. There will be not many people and hopeless cases liked to be tried. It is a good history how all the cases got in the collection and prove for the final answer: there was a process time of detoxing through the skin. It became less and less until all the body's waste was pushed through the skin pores. The healing takes place for all kind of chronic infection, disease, health issue, and skin problems, which is all great news. This discovery was adding up and the problems were solved.

There is no need to worry and be stressed when a new case is discovered because the detox detoxing can cure the skin. It may be too late to stop this process, but at least it can explain the experience with the unsuccessful treatment happening in many cases before. The experience shows how to provide the best advice to deal with or prevent these outcomes. Much more respect and appreciation is now received for all experience that was gained over the years.

Many people received great news when they had their blood tested in a checkup, which was a big surprise for all diseases such as: cholesterol, diabetes, and hepatitis A, B and C. The doctor reported the healing and was much surprised by the results. Many cases need no more of the drugs or pills for diabetes and cholesterol. Many cases were healing, and the cure was a great experience and discovery. After 20 years with all the collection observed in the groups of viruses, flu infection and chronic infections, the treatment can be used and works well for Covid-19. It will be a surprise to the world how diseases, bacteria, and viruses can be treated in a simple way. A turmeric syrup trap for all.

The discovery of the trap is a treatment for many issues which can result in healing, recovering and cure. The whitened turmeric products natural based medicine.

Also, work has been done with a lot of turmeric plants, some root was a choice for the whitened turmeric base. And testing was done on two special kinds which have the natural white color root. By testing and conducting research on these white roots, it was found that it works and has a similar benefit treatment compared to the whitened turmeric product. These roots are growing much more in a garden, but they are not ready yet for public use, but can be added to the base, mixed with the whitened turmeric base and the ingredients for all turmeric product, which will also be used as a treatment for Covid-19.

The invention claimed is:

1. A method of treating a viral infection for a person in need thereof, the method comprising:
   administering a whitened turmeric product in an effective amount to a person;
   trapping the virus causing the viral infection with the whitened turmeric product; and
   preventing a spread of the virus to the person and from the person to other people,
   wherein the virus is a Coronavirus causing Covid-19, and
   wherein 5 to 10 drops of the whitened turmeric product are applied to the throat after a meal.

2. The method of claim 1, wherein the amount of the whitened turmeric product is selected to further treat at least one of a cough, sneeze, running nose, and infection of the lung.

3. The method of claim 1, wherein the method is further used for pain relief, reducing the swelling, healing, and recovering of the infection area in the mouth and/or throat.

4. The method of claim 1, wherein the treatment helps a body detox, or blood cleanser in the treatment for coronavirus.

* * * * *